United States Patent
Das et al.

(10) Patent No.: US 10,719,945 B2
(45) Date of Patent: Jul. 21, 2020

(54) SYSTEM AND METHOD FOR FACE POSITION TRACKING AND ALERTING USER

(71) Applicant: Tata Consultancy Services Limited, Mumbai (IN)

(72) Inventors: Apurba Das, Bangalore (IN); Nithish Chauhan, Bangalore (IN); Hardik Jayesh Sanghani, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 262 days.

(21) Appl. No.: 16/030,559

(22) Filed: Jul. 9, 2018

(65) Prior Publication Data
US 2019/0139233 A1 May 9, 2019

(30) Foreign Application Priority Data
Nov. 7, 2017 (IN) .............................. 201721039668

(51) Int. Cl.
*G06K 9/00* (2006.01)
*G06T 7/246* (2017.01)
(Continued)

(52) U.S. Cl.
CPC ................ *G06T 7/251* (2017.01); *A61B 5/18* (2013.01); *B60K 28/02* (2013.01); *B60K 28/06* (2013.01);
(Continued)

(58) Field of Classification Search
CPC .......... G06K 9/00221; G06K 9/00228; G06K 9/00248; G06K 9/00261; G06K 9/00268;
(Continued)

(56) References Cited

U.S. PATENT DOCUMENTS 6,246,779 B1 * 6/2001 Fukui ................ G06K 9/00268
382/100
8,040,247 B2 * 10/2011 Gunaratne ......... G06K 9/00221
340/5.83
(Continued)

FOREIGN PATENT DOCUMENTS

EP          2371649 B1    10/2011

OTHER PUBLICATIONS

Mira Jeong, Joon Young Kwak, Byoung Chul Ko, Jaeyeal Nam, "Facial landmark detection based on an ensemble of local weighted regressors during real driving situation", IEEE, 23rd International Conference on Pattern Recognition (ICPR), 2016, pp. 2198-2203 (Year: 2016).*
(Continued)

*Primary Examiner* — Eric Rush
(74) *Attorney, Agent, or Firm* — Finnegan, Henderson, Farabow, Garrett & Dunner LLP (57) ABSTRACT

Current technologies detect the alertness of a user using frontal face. However, there are no techniques to track the position of face from a side angle. A method and system for face position tracking of a user and alerting the user is disclosed. The method includes capturing images using a monocular camera and identifying a user's face from the images and storing the user's face as reference face. The user's face is divided into two regions and one or more corner points are identified. A centroid is created in the two regions and the corner points are joined using virtual lines to create a dual flexible spider model. One or more new corner points are created on fulfillment of pre-defined conditions. Angle and magnitude of flow vectors is determined using one or more new corner points and alerts are given to the user based on the angle and magnitude.

19 Claims, 6 Drawing Sheets

(51) Int. Cl.
| | |
|---|---|
| *G08B 21/06* | (2006.01) |
| *G06T 7/149* | (2017.01) |
| *B60K 28/06* | (2006.01) |
| *G06K 9/46* | (2006.01) |
| *G06K 9/62* | (2006.01) |
| *G06T 7/73* | (2017.01) |
| *G06T 7/181* | (2017.01) |
| *B60K 28/02* | (2006.01) |
| *G06T 7/162* | (2017.01) |
| *A61B 5/18* | (2006.01) |
| *G06F 3/01* | (2006.01) |

(52) U.S. Cl.
CPC ............ *B60K 28/066* (2013.01); *G06F 3/012* (2013.01); *G06K 9/00228* (2013.01); *G06K 9/00248* (2013.01); *G06K 9/00281* (2013.01); *G06K 9/00288* (2013.01); *G06K 9/00335* (2013.01); *G06K 9/00362* (2013.01); *G06K 9/468* (2013.01); *G06K 9/4638* (2013.01); *G06K 9/6211* (2013.01); *G06K 9/6261* (2013.01); *G06T 7/149* (2017.01); *G06T 7/162* (2017.01); *G06T 7/181* (2017.01); *G06T 7/246* (2017.01); *G06T 7/73* (2017.01); *G06T 7/75* (2017.01); *G08B 21/06* (2013.01); *G06K 9/00845* (2013.01); *G06T 2207/20024* (2013.01); *G06T 2207/20164* (2013.01); *G06T 2207/20192* (2013.01); *G06T 2207/30201* (2013.01); *G06T 2207/30268* (2013.01)

(58) Field of Classification Search
CPC ........... G06K 9/00281; G06K 9/00288; G06K 9/00335; G06K 9/00362; G06K 9/00832; G06K 9/00845; G06K 9/46; G06K 9/4604; G06K 9/4638; G06K 9/468; G06K 9/469; G06K 9/525; G06K 9/6202; G06K 9/6206; G06K 9/6209; G06K 9/6211; G06K 9/6261; G06T 7/00; G06T 7/149; G06T 7/162; G06T 7/181; G06T 7/20; G06T 7/246; G06T 7/248; G06T 7/251; G06T 7/60; G06T 7/66; G06T 7/70; G06T 7/73; G06T 7/74; G06T 7/75; G06T 2207/20024; G06T 2207/20164; G06T 2207/20192; G06T 2207/30201; G06T 2207/30268; G08B 21/06; B60K 28/02; B60K 28/06; B60K 28/066; G06F 3/012; A61B 5/11; A61B 5/1103; A61B 5/16; A61B 5/153; A61B 5/18; H04N 13/366; H04N 13/371; H04N 13/373; H04N 13/376; H04N 13/378; H04N 13/38
USPC ........ 382/100, 103, 104, 115, 117, 118, 181, 382/190, 193, 195, 197, 199, 202, 203, 382/215–218, 288, 291; 348/77, 148, 348/169–172; 702/150–153
See application file for complete search history.

(56) References Cited

U.S. PATENT DOCUMENTS

| | | | | |
|---|---|---|---|---|
| 9,898,836 | B2* | 2/2018 | Hsieh | G06K 9/00248 |
| 10,089,543 | B2* | 10/2018 | Fung | G06K 9/00302 |
| 2007/0159344 | A1* | 7/2007 | Kisacanin | G06K 9/00362 |
| | | | | 340/576 |
| 2011/0249868 | A1* | 10/2011 | Tsukizawa | G06K 9/00604 |
| | | | | 382/103 |
| 2012/0242819 | A1* | 9/2012 | Schamp | G06K 9/00228 |
| | | | | 348/78 |
| 2015/0296135 | A1 | 10/2015 | Wacquant et al. | |

OTHER PUBLICATIONS

K. Dwivedi, et al., "Drowsy Driver Detection using Representation Learning," *2014 IEEE International Advanced Computing Conference (IACC)*, Feb. 21-22, 2014, Gurgaon, India; 5 pages.

* cited by examiner

SYSTEM AND METHOD FOR FACE POSITION TRACKING AND ALERTING USER

PRIORITY CLAIM

This U.S. patent application claims priority under 35 U.S.C. § 119 to: India Application No. 201721039668, filed on 2017 Nov. 7. The entire contents of the aforementioned application are incorporated herein by reference.

TECHNICAL FIELD

The disclosure herein generally relate to tracking face of a user, and more particularly, system and method for face position tracking of a user and alerting the user.

BACKGROUND

Determining the alertness of a user is one of the areas for research. One of the examples for determining the alertness is a driver in a vehicle using. Fatalities have occurred as a result of car accidents related to driver inattention, such as fatigue and lack of sleep. Physiological feature-based approaches are intrusive because the measuring equipment must be attached to the driver. Physiological feature based approaches utilize visual technologies to determine the alertness of the user. Thus, physiological feature-based approaches have recently become preferred because of their non-intrusive nature.

The existing models of driver alertness monitoring (DAM) system relies on detection of frontal face using a camera that is placed in front of the driver. Most of the existing methods use CAMSHIFT algorithms that rely on the skin color. Therefore, tracking is efficient in day light. The other problem with optical flow tracking is the key points on the face always tends to be missed if there is jerk in driving. The optical flow tracking is not so reliable if someone rubs hand over the face. The key points in a face are dragged by the hand showing wrong alert.

SUMMARY

Embodiments of the present disclosure present technological improvements as solutions to one or more of the above-mentioned technical problems recognized by the inventors in conventional systems. For example, in one embodiment, a method for face position tracking and alerting user is disclosed. The method includes capturing one more images through a monocular camera. The method further includes identifying a user's face from the one or more face identified in the one or more images. Further, divining the identified the user's face into a first region and a second region and identifying one or more corner points in each of the first region and the second region. A centroid is created in each of the first region and the second region and joining the one or more corner points with each of the centroid with a plurality of virtual lines to create dual flexible spider model. Subsequently, the plurality of lines are created dense in the dual flexible spider model. The variations in the dual flexible spider model due to movement of user's face is tracked based on the magnitude and the phase value of the one or more corner points. Subsequently, one or more new corner points and one or more flow vectors are created by subjecting the one or more new corner points to the optical flow frame. Further one or more valid motion vectors, one or more invalid motion vectors and one or more static motion vectors are determined based on angle and magnitude of the one or more flow vectors. The user is given an alert if the angle and magnitude of the one or more valid motion vectors is greater than a threshold.

In another embodiment, a system for face position tracking and alerting the user is disclosed. The system includes at least one processor, and a memory communicatively coupled to the at least one processor, wherein the memory comprises of several modules. The modules includes face tracking module that captures one or more images. Further a user's face is identified from the one or more face identified in the one or more images. Further, divining the identified the user's face into a first region and a second region and identifying one or more corner points in each of the first region and the second region. A centroid is created in each of the first region and the second region and joining the one or more corner points with each of the centroid with a plurality of virtual lines to create dual flexible spider model. Subsequently, the plurality of lines are created dense in the dual flexible spider model. The variations in the dual flexible spider model due to movement of user's face is tracked based on the magnitude and the phase value of the one or more corner points. Subsequently, one or more new corner points and one or more flow vectors are created by subjecting the one or more new corner points to the optical flow frame. Further one or more valid motion vectors, one or more invalid motion vectors and one or more static motion vectors are determined based on angle and magnitude of the one or more flow vectors. The user is given an alert if the angle and magnitude of the one or more valid motion vectors is greater than a threshold.

In yet another aspect, a non-transitory computer-readable medium for face position tracking and alerting user is disclosed. The non-transitory computer-readable medium stores instructions which, when executed by hardware processor, causes the hardware processor to perform acts comprising capturing one more images through a monocular camera. The acts further include identifying a user's face from the one or more face identified in the one or more images. Further the act includes, divining the identified the user's face into a first region and a second region and identifying one or more corner points in each of the first region and the second region. A centroid is created in each of the first region and the second region and joining the one or more corner points with each of the centroid with a plurality of virtual lines to create dual flexible spider model. Subsequently, the plurality of lines are created dense in the dual flexible spider model. The variations in the dual flexible spider model due to movement of user's face is tracked based on the magnitude and the phase value of the one or more corner points. Subsequently, one or more new corner points and one or more flow vectors are created by subjecting the one or more new corner points to the optical flow frame. Further the act include one or more valid motion vectors, one or more invalid motion vectors and one or more static motion vectors are determined based on angle and magnitude of the one or more flow vectors. The user is given an alert if the angle and magnitude of the one or more valid motion vectors is greater than a threshold.

It is to be understood that both the foregoing general description and the following detailed description are explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 (FIG. 3(a) and FIG. 3(b)) is an example of the dual flexible spider model of a driver in the car, according to some embodiments of the present subject matter;

FIG. 4 (FIG. 4(a) and FIG. 4(b)) is an example of user interface for alerting the user, according to some embodiments of the present subject matter; and FIG. 5 (FIG. 5(a) and FIG. 5(b)) is a flow chart illustrating a method for face position tracking and alerting the user, according to some embodiments of the present subject matter.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The manner in which the described system is implemented for face position tracking and alerting the user has been explained in detail with respect to the following figure(s). While aspects of the described system can be implemented in any number of different computing systems, transmission environments, and/or configurations, the embodiments are described in the context of the following exemplary system.

Figure 1:
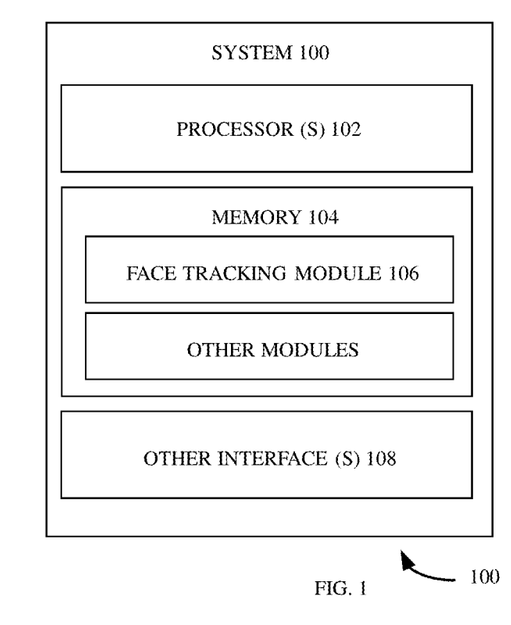
FIG. 1 illustrates a system for face position tracking and alerting user, according to some embodiments of the present disclosure.

FIG. 1 schematically illustrates a system 100 for face position tracking of a user and alerting the user, according to an embodiment of the present disclosure. As shown in FIG. 1, the system 100 includes one or more processor(s) 102 and a memory 104 communicatively coupled to each other. The memory 104 includes a face tracking module 106 that tracks the face position of the user and alert the user. The system 100 also includes interface(s) 108. Although FIG. 1 shows example components of the system 100, in other implementations, the system 100 may contain fewer components, additional components, different components, or differently arranged components than depicted in FIG. 1.

The processor(s) 102 and the memory 104 may be communicatively coupled by a system bus. The processor(s) 102 may include circuitry implementing, among others, audio and logic functions associated with the communication. The processor 102 may include, among other things, a clock, an arithmetic logic unit (ALU) and logic gates configured to support operation of the processor(s) 102. The processor(s) 102 can be a single processing unit or a number of units, all of which include multiple computing units. The processor(s) 102 may be implemented as one or more microprocessors, microcomputers, microcontrollers, digital signal processors, central processing units, state machines, logic circuitries, and/or any devices that manipulate signals based on operational instructions. Among other capabilities, the processor(s) 102 is configured to fetch and execute computer-readable instructions and data stored in the memory 104.

The functions of the various elements shown in the figure, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional, and/or custom, may also be included.

The interface(s) 108 may include a variety of software and hardware interfaces, for example, interfaces for peripheral device(s), such as a keyboard, a mouse, an external memory, and a printer. The interface(s) 108 can facilitate multiple communications within a wide variety of networks and protocol types, including wired networks, for example, local area network (LAN), cable, etc., and wireless networks, such as Wireless LAN (WLAN), cellular, or satellite. For the purpose, the interface(s) 108 may include one or more ports for connecting the system 100 to other network devices.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 104, may store any number of pieces of information, and data, used by the system 100 to track face positioning of user's face and alerting the user. The memory 104 may be configured to store information, data, applications, instructions or the like for system 100 to carry out various functions in accordance with various example embodiments. Additionally or alternatively, the memory 104 may be configured to store instructions which when executed by the processor 102 causes the system 100 to behave in a manner as described in various embodiments. The memory 104 includes the face tracking module 106 and other modules. The face tracking module 106 include routines, programs, objects, components, data structures, etc., which perform particular tasks or implement particular abstract data types.

In an embodiment, a method for tracking face position of a user and alerting the user in case the face is diverted from an original position is disclosed. The face tracking module 106 captures one or more images using a camera. The camera is positioned at an angle from a user's face. For example, in a car, to track face position of a driver, a monocular camera can be placed to A-pillar of the car. Therefore the monocular camera captures the images from a side angle of the driver instead of capturing images from the front angle.

Subsequently, if there are more than one person in the one or more images, one or more faces are identified from the one or more images captured and a user's face is identified based on space occupied in the one or more images. The face occupying more space is considered as the user's face for tracking face position of the user. In this method the one or more faces are detected using the haar cascade classifier algorithm and a confidence score is given to bigger face. For example, in the case of determining the face position of the driver in a car the space occupied is more because the driver will be more close to the camera than other faces in the car. The user's face is stored as a reference face for future comparison.

In an embodiment, the user's face is divided into two regions, namely a first region and a second region. For example, the user's face can be divided into a left region and a right region. The face tracking module 106 further identifies one or more corner points from the first region and the second region of the user's face. The one or more corner points are identified by finding a rough position of the user's face using a face detector. The one or more corner points are determined based on intensity of light falling on the user's face.

In an embodiment, the face tracking module 106 uses deformable part model (DPM) on low resolution face to refine the position of the user's face detected. Subsequently finding features sparsely on the high resolution image using different DPM in required region of interest of the user's face.

Figure 2:
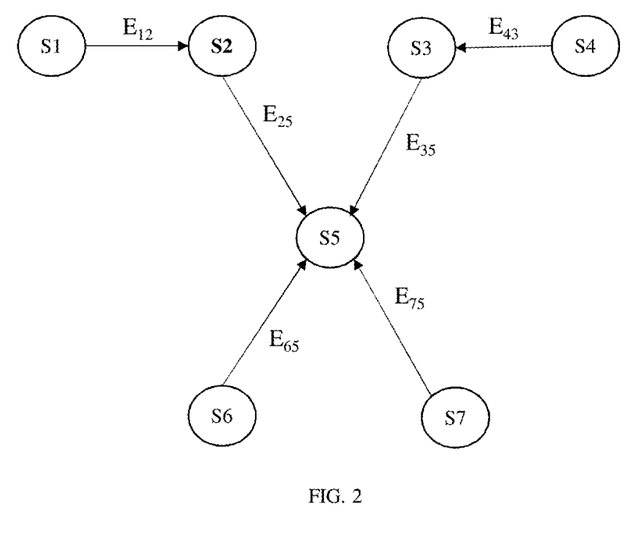
FIG. 2 is an example of tree based representation of deformable pattern model (DPM), according to some embodiments of the present subject matter.

FIG. 2 is an example of tree based representation of deformable pattern model (DPM), according to some embodiments of the present subject matter. FIG. 2 is an example of tree based unidirectional representation of DPM, where one or more nodes of the tree represent the one or more corner points depicting the local features and the edges connecting them gives the relative position with respect to neighboring corner points.

The tree graph is computed based on the equation, tree graph G=(V, E)

The example contains seven vertices S1 to S7 are the one or more corner points and $E_{12}, E_{25}, E_{43}, E_{35}, E_{75}, E_{65}$ are the six edges connecting the vertices S1 to S7.

$$F(I,s)=\Sigma_{i=v}q_i(I,s_i)+\Sigma_{(i,j)=E}g(s_i,s_j)$$

Where first term corresponds to the match between position of the key point si and image I. It represents the quality of fit of one or more corner points. Second term corresponds to deformation cost determining the relative position of the two corner points.

Figures 3, 3A, 3B:
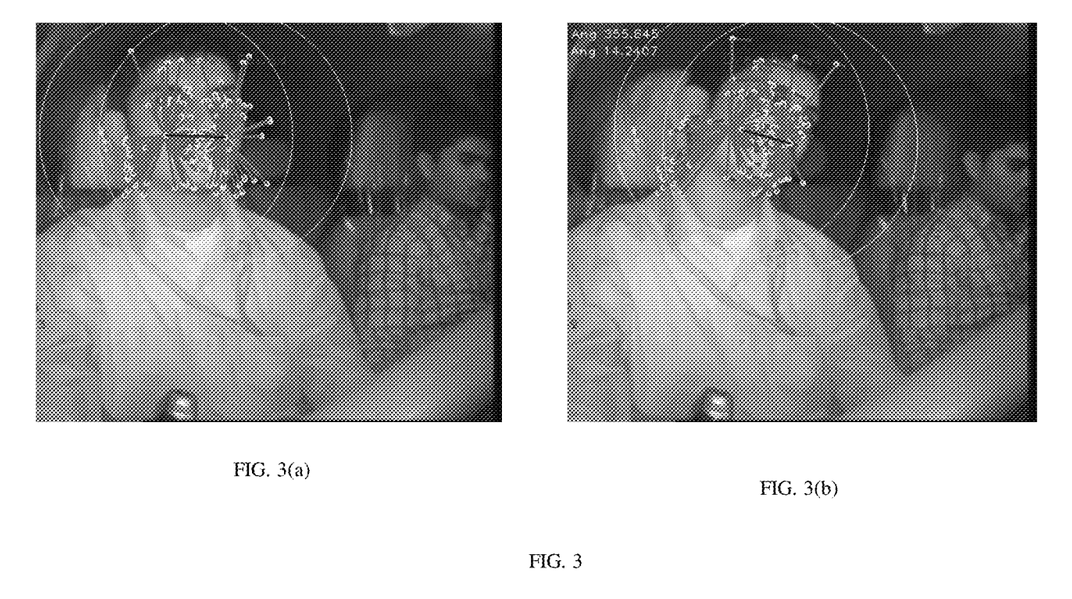

In an embodiment, the face tracking module 106 creates a centroid in each of the first region and the second region. The centroid in each of the first region and the second region are joined with the respective one or more corner points using a plurality of virtual lines to create a dual flexible spider model. FIG. 3 (FIG. 3a and FIG. 3b) is an example of the dual flexible spider model of a driver in the car, according to some embodiments of the present subject matter.

In an embodiment, a method for creating a plurality of virtual lines dense in the dual flexible spider model is disclosed. If the user's face is attentive for a pre-defined time period, one or more corner points are increased. The face tracking module 106 increases one or more corner points by equalizing face region and applying a laplacian filter to enhance edges. The increased edges increase the one or more corner points. The method further joins the centroid with the increased respective one or more corner points to create the plurality of virtual lines dense in the dual flexible spider model.

In an embodiment, when the position of the user's face changes from one position to other position, new corner points are created.

In an embodiment, a reset logic is added to create one or more new corner points in continuous tracking that if any of the following conditions are satisfied. The conditions on which a reset logic is utilized are:
(i) the user's face is not visible or (ii) the one or more virtual lines are not handling the face due to fast movement or (iii) deviation of the user's face is greater than a threshold.

The one or more new corner points are location coordinates of the corner points of the user's face. Therefore, the one or more new corner points are subjected to optical flow frame pair wise.

The face tracking module 106 calculates angle and magnitude of the flow vectors obtained from the optical flow for each transition between each pair of frames. The face tracking module 106 further describes the continuous head motion based on the position of the one or more new corner points. The flow vectors are very fragile and disperse with small variation in motion such as jerk or inadvertent motion such as driver hand movements while driving. The flow vectors are divided into three types.

Based on the angle and magnitude of the one or more flow vector points, the one or more flow vectors can be classified into three groups a) Valid Motion Vectors b) Invalid Motion Vectors and c) Static Vectors.

One or more valid motion vectors are the flow vectors if the magnitude of the one or more flow vectors is within a predefined magnitude or the plurality of virtual lines are moving in same direction or exhibit homogeneous scaling or there is co-presence of vectors. One or more invalid motion vectors are the one or more flow vectors if the magnitude of the one or more flow vectors is greater than the predefined magnitude or the plurality of virtual lines are not moving in same direction or do not exhibit homogeneous scaling or there is no co-presence of vectors and one or more static motion vectors are the one or more flow vectors if the magnitude of the one or more flow vectors is constant.

In an embodiment, the face tracking module 106 considers one or more valid motion vectors for further process. The invalid motion vectors and static motion vectors are not considered for tracking and giving an alarm to the user.

In an embodiment, different scenarios for giving an alert to the user are disclosed. In an embodiment, the face tracking module 106 considers the dual spider model of the valid motion vectors. The angle and magnitude caused due to change in the position of the virtual lines for the valid motion vectors is considered. If the angle and magnitude of the virtual lines is greater than threshold, then an alarm is given. However, if the angle and magnitude of the virtual lines of the dual spider is less than the threshold then an alarm is not given.

In another embodiment, an alarm is given when the user's face is not visible.

In an embodiment, the face tracking module 106 captures the user's face and matches the user's face with the reference face. If the user's face is not matching with the reference face, the user is not attentive and a first alert is given to the user. A second alert is given if the user is not matching with the reference face after the first alert.

Figures 4, 4A, 4B:
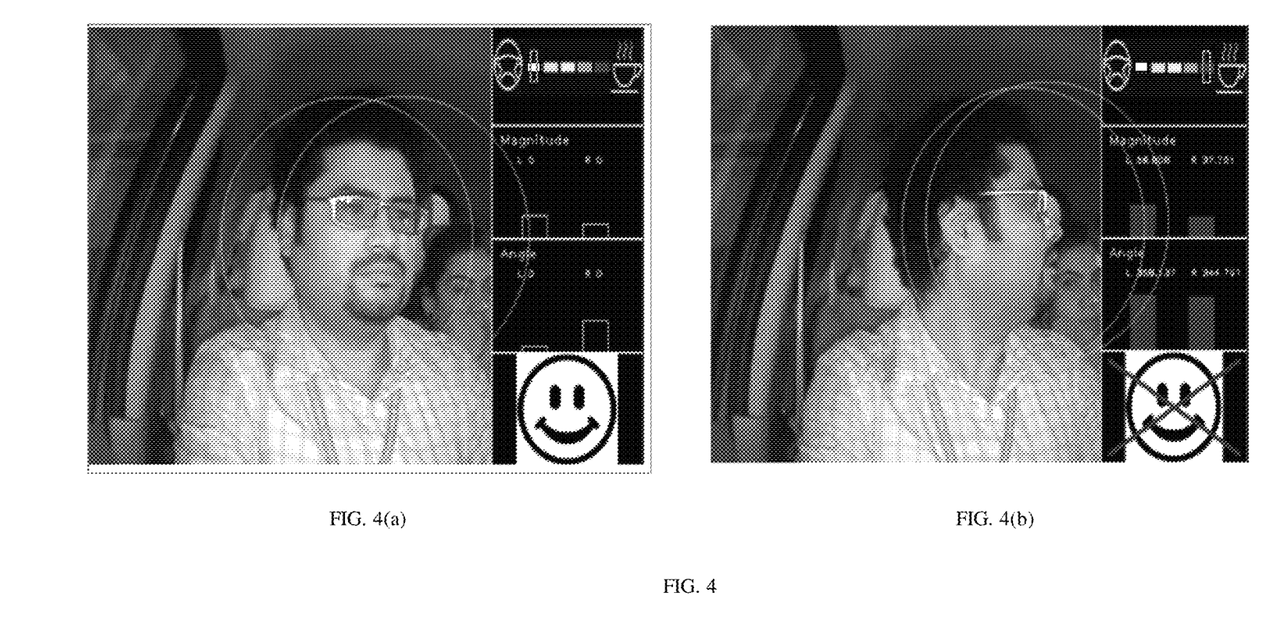

FIG. 4 is an example of user interface for alerting the user, according to some embodiments of the present subject matter. FIG. 4(a) is an example of user interface when the user is alert. A threshold for magnitude and angle is provided by the user. The angle and magnitude is within the threshold as the user is alert. An emoticon in FIG. 4(a) is indicating that the user is alert. In FIG. 4(b), the user is not alert. The angle and magnitude of flow vectors in the FIG. 4(b) has reached the threshold values. The emoticon in the FIG. 4(b) is indicating that the user is not visible.

In an embodiment, if the user's face is attentive for the predefined time period, the magnitude and the phase value is reset to avoid a false alert due to accumulation of noisy movements.

In an embodiment, the situations for false alerts are considered. The false alerts are caused if the driver is moving head such that he is not feeling sleepy but just not attentive, then there is (small) valid motion flow vector magnitude additions and the magnitude of flow vectors can sometimes be greater than threshold giving false alarms.

In order to address the false alarm problem, the face tracking module 106 comprises a periodic timer co-relator. The periodic timer co-relator frequently checks if the reference face is matching with the user's face that is created with the one or more new corner points. If the face is matched at predefined intervals of time then it means that the user is looking and the magnitudes of VM Vectors can be reset to remove invalid vector additions to eliminate false alarms. If the face is not matched properly after predefined intervals, then one or more new corner points are considered.

Similarly if the user falls asleep in the same position without head movement, the system 100 will not give the alarm. Therefore, to determine the alertness of the user when there is no head movement, the face tracking module 106 detects the eyes of the driver. If the eyes are detected then no alarm is raised and if the eyes of the user are detected, then alarm is raised and one or more new corner points are considered.

Figure 5A:
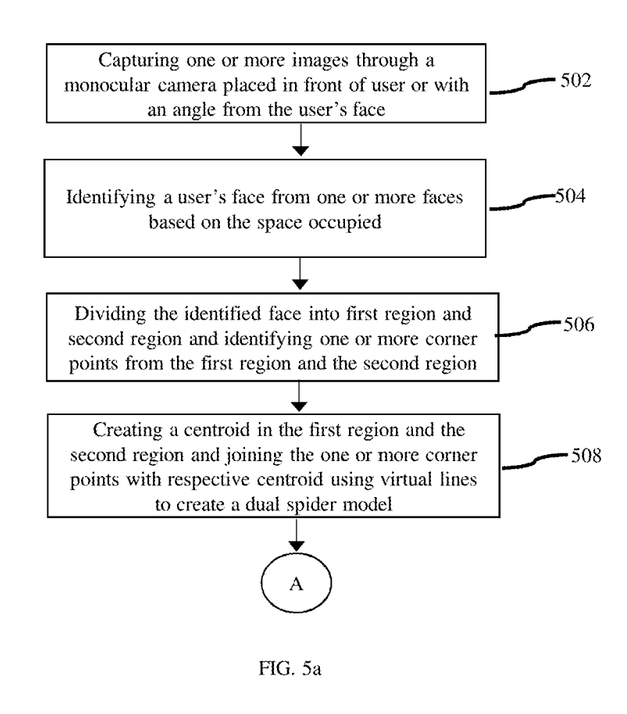
Figure 5B:
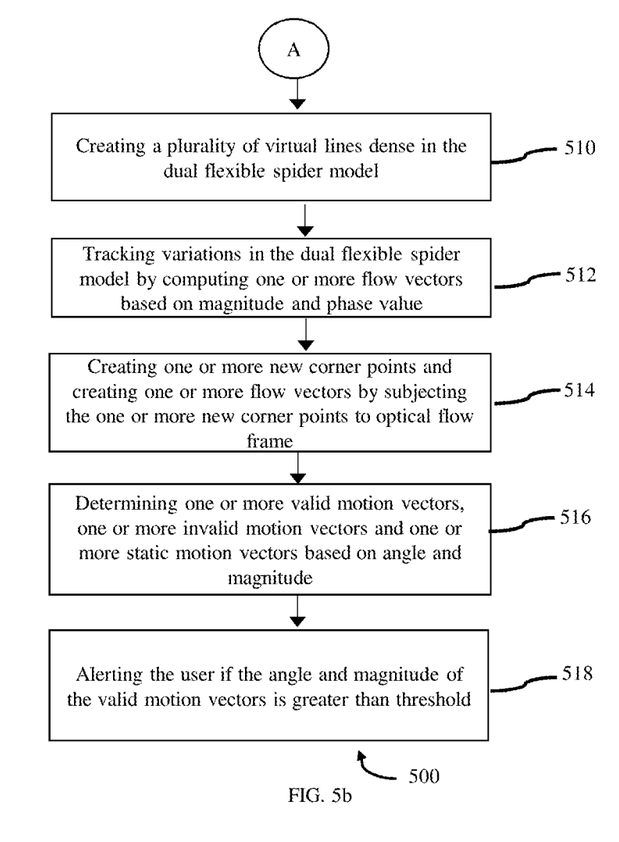

FIG. 5 (FIG. 5(a) and FIG. 5(b)) is a flow chart illustrating a method for face position tracking of a user and alerting the user, according to some embodiments of the present subject matter. At block 502, one or more images are captured through a camera. At block 504, a user's face is identified from one or more face identified in the one or more images. At block 506, the user's face is divided into a first region and second region and one or more corner points are identified from the first region and the second region. At block 508, a centroid in each of the first region and the second region is created and joining the centroid with one or more corner points using virtual lines to create a dual flexible spider model. At block 510, a plurality of virtual lines are created dense in the dual flexible spider model. At block 512, variations in the dual flexible spider model are tracked by computing one or more flow vectors. At block 514, one or more new corner points are created and one or more flow vectors are created by subjecting the one or more new corner points to optical flow frame. At block 516, one or more valid motion vectors, one or more invalid motion vectors and one or more static vectors are determined. At block 518, the user is given an alert if the angle and magnitude of the valid motion vectors is greater than threshold.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant arts based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims

What is claimed is:

1. A method for face position tracking and alerting a user, the method comprising:
    capturing one or more images through a camera;
    identifying the user's face from one or more faces based on space occupied in the one or more images to store the user's face as a reference face;
    dividing the user's face into (i) a first region and (ii) a second region and identifying one or more corner points from the first region and the second region of the user's face;
    creating a centroid in each of the first region and the second region and joining the one or more corner points with the centroid created in each of the first region and the second region using a plurality of virtual lines to create a dual flexible spider model;
    creating a dense plurality of virtual lines in the dual flexible spider model, based on movement of the user's face for a predefined time period;
    tracking variations in the dual flexible spider model due to the movement of the user's face by computing one or more flow vectors based on a magnitude and a phase value of the one or more corner points;
    creating one or more new corner points and creating one or more additional flow vectors by subjecting the one or more new corner points to optical flow frame processing, wherein the one or more new corner points are created based on one or more predefined conditions;
    determining one or more valid motion vectors, one or more invalid motion vectors and one or more static motion vectors based on an angle and magnitude of the one or more flow vectors; and
    alerting the user if the angle and magnitude of the one or more flow vectors of the one or more valid motion vectors is greater than a threshold.

2. The method of claim 1, wherein if the user's face is attentive for the predefined time period, the magnitude and the phase value of the one or more corner points is reset to avoid a false alert due to accumulation of noisy movements.

3. The method of claim 1, wherein the one or more valid motion vectors are the one or more flow vectors if (i) the magnitude of the one or more flow vectors is within a predefined magnitude or (ii) the plurality of virtual lines are moving in a same direction or exhibit homogeneous scaling or there is co-presence of vectors.

4. The method of claim 1, wherein the one or more invalid motion vectors are the one or more flow vectors if (i) the magnitude of the one or more flow vectors is greater than a predefined magnitude or (ii) the plurality of virtual lines are not moving in a same direction or do not exhibit homogeneous scaling or there is no co-presence of vectors.

5. The method of claim 1, wherein the one or more static motion vectors are the one or more flow vectors if the magnitude of the one or more flow vectors is constant.

6. The method of claim 1, wherein identifying the user's face based on the space occupied in the one or more images is performed using a haar cascade classifier algorithm.

7. The method of claim 1, wherein creating the dense plurality of virtual lines includes equalizing a face region and applying a laplacian filter to enhance edges of the user's face and create the dense plurality of virtual lines.

8. The method of claim 1, wherein the one or more predefined conditions are (i) the user's face is not visible or (ii) the plurality of virtual lines are not handling the user's face due to fast movement or (iii) deviation of the user's face is greater than a threshold.

9. A system for face position tracking and alerting a user, the system comprising:
    at least one processor; and
    a memory communicatively coupled to the at least one processor, wherein the memory comprises
    a face tracking module instructing the at least one processor to:
        capture one or more images through a camera;
        identify the user's face from one or more faces based on space occupied in the one or more images to store the user's face as a reference face;
        divide the user's face into (i) a first region and (ii) a second region and identify one or more corner points from the first region and the second region of the user's face;
        create a centroid in each of the first region and the second region and join the one or more corner points with the centroid created in each of the first region and the second region using a plurality of virtual lines to create a dual flexible spider model;
        create a dense plurality of virtual lines in the dual flexible spider model, based on movement of the user's face for a predefined time period;
        track variations in the dual flexible spider model due to the movement of the user's face by computing one or more flow vectors based on a magnitude and a phase value of the one or more corner points;
        create one or more new corner points and create one or more additional flow vectors by subjecting the one or more new corner points to optical flow frame processing, wherein the one or more new corner points are created based on one or more predefined conditions;
        determine one or more valid motion vectors, one or more invalid motion vectors and one or more static motion vectors based on an angle and magnitude of the one or more flow vectors; and
        alert the user if the angle and magnitude of the one or more flow vectors of the one or more valid motion vectors is greater than a threshold.

10. The system of claim 9, wherein if the user's face is attentive for the predefined time period, the magnitude and the phase value of the one or more corner points is reset to avoid a false alert due to accumulation of noisy movements.

11. The system of claim 9, wherein the one or more valid motion vectors are the one or more flow vectors if the magnitude of the one or more flow vectors is within a predefined magnitude or the plurality of virtual lines are moving in a same direction or exhibit homogeneous scaling or there is co-presence of vectors.

12. The system of claim 9, wherein the one or more invalid motion vectors are the one or more flow vectors if the magnitude of the one or more flow vectors is greater than a predefined magnitude or one or more of the plurality of virtual lines are not moving in a same direction or do not exhibit homogeneous scaling or there is no co-presence of vectors.

13. The system of claim 9, wherein the one or more static motion vectors are the one or more flow vectors if the magnitude of the one or more flow vectors is constant.

14. The system of claim 9, wherein identifying the user's face based on the space occupied in the one or more images is performed using haar cascade classifier algorithm.

15. The system of claim 9, wherein creating the dense plurality of virtual lines includes equalizing a face region and applying a laplacian filter to enhance edges and create the dense plurality of virtual lines.

16. The system of claim 9, wherein the one or more predefined conditions are (i) the user's face is not visible or (ii) the plurality of virtual lines are not handling the user's face due to fast movement or (iii) deviation of the user's face is greater than a threshold.

17. A non-transitory computer-readable medium storing instructions which, when executed by a hardware processor, cause the hardware processor to perform acts comprising:
    capturing one or more images through a camera;
    identifying a user's face from one or more faces based on space occupied in the one or more images to store the user's face as a reference face;
    dividing the user's face into (i) a first region and (ii) a second region and identifying one or more corner points from the first region and the second region of the user's face;
    creating a centroid in each of the first region and the second region and joining the one or more corner points with the centroid created in each of the first region and the second region using a plurality of virtual lines to create a dual flexible spider model;
    creating a dense plurality of virtual lines in the dual flexible spider model, based on movement of the user's face for a predefined time period;
    tracking variations in the dual flexible spider model due to the movement of the user's face by computing one or more flow vectors based on a magnitude and a phase value of the one or more corner points;
    creating one or more new corner points and creating one or more additional flow vectors by subjecting the one or more new corner points to optical flow frame processing, wherein the one or more new corner points are created based on one or more predefined conditions;
    determining one or more valid motion vectors, one or more invalid motion vectors and one or more static motion vectors based on an angle and magnitude of the one or more flow vectors; and
    alerting the user if the angle and magnitude of the one or more flow vectors of the one or more valid motion vectors is greater than a threshold.

18. The non-transitory computer-readable medium of claim 17, wherein if the user's face is attentive for the predefined time period, the magnitude and the phase value of the one or more corner points is reset to avoid a false alert due to accumulation of noisy movements.

19. The non-transitory computer-readable medium of claim 17, wherein the one or more valid motion vectors are the one or more flow vectors if (i) the magnitude of the one or more flow vectors is within a predefined magnitude or (ii) the plurality of virtual lines are moving in a same direction or exhibit homogeneous scaling or here is co-presence of vectors.

* * * * *